US012773337B2

(12) United States Patent
Lin

(10) Patent No.: US 12,773,337 B2
(45) Date of Patent: Oct. 27, 2026

(54) DEVICE FOR FASTENING A THUMB AND METHOD THEREFOR

(71) Applicant: CHUNG SHAN MEDICAL UNIVERSITY HOSPITAL, Taichung City (TW)

(72) Inventor: Sheng-Chieh Lin, Taichung City (TW)

(73) Assignee: CHUNG SHAN MEDICAL UNIVERSITY HOSPITAL, Taichung City (TW)

( * ) Notice: Subject to any disclaimer, the term of this patent is extended or adjusted under 35 U.S.C. 154(b) by 15 days.

(21) Appl. No.: 18/927,831

(22) Filed: Oct. 25, 2024

(65) Prior Publication Data

US 2025/0134689 A1 May 1, 2025

(30) Foreign Application Priority Data

Oct. 31, 2023 (TW) ................................ 112141745

(51) Int. Cl.
*A61F 5/01* (2006.01)

(52) U.S. Cl.
CPC .................................. *A61F 5/0118* (2013.01)

(58) Field of Classification Search
CPC .... A61F 5/0118; A61F 5/013; A61F 5/05866; A61F 5/05858; A61F 5/05841; A61F 5/058; A61F 5/05; A61F 5/04; A61F 5/01; A61F 2005/0186; A61F 5/05875; A61F 5/10; A61F 5/50; A61H 1/0288; A61H 2205/067
See application file for complete search history.

(56) References Cited

U.S. PATENT DOCUMENTS

| | | | | |
|---|---|---|---|---|
| 6,110,136 | A * | 8/2000 | Belkin | A61F 5/05866 128/880 |
| 11,547,356 | B2 | 1/2023 | Kwok et al. | |
| 2012/0289877 | A1* | 11/2012 | Hegland | A61F 5/013 602/22 |
| 2021/0267782 | A1* | 9/2021 | Kienzle | B33Y 80/00 |
| 2022/0079639 | A1 | 3/2022 | Jang et al. | |

* cited by examiner

*Primary Examiner* — Victoria Hicks Fisher
(74) *Attorney, Agent, or Firm* — Cheng-Ju Chiang

(57) ABSTRACT

A device for fastening a thumb includes a first tubular member including a first elliptical hole having first major and minor axes; a second tubular member including a second elliptical hole having second major and minor axes; a length of the second major axis is greater than that of the first major axis and the second major axis is perpendicular to the first major axis, the second elliptical hole is perpendicular to the first elliptical hole, and a length of the second minor axis is greater than that of the first minor axis; and an intermediate joint including a fastener. When the device is disposed on the thumb, the first tubular member is disposed on the distal phalanx, the second tubular member is disposed on the proximal phalanx, and the fastener presses the interphalangeal joint to prevent the interphalangeal joint from being bent.

2 Claims, 6 Drawing Sheets

DEVICE FOR FASTENING A THUMB AND METHOD THEREFOR

FIELD OF THE INVENTION

The invention relates to fastening devices and more particularly to a device for fastening a thumb and method therefor. This invention has the advantages of customized three-dimensional (3D) printing, high precision, convenience, single handed operation, and non-binding correction.

BACKGROUND OF THE INVENTION

A conventional device for fastening a thumb is shown in FIG. 9 and comprises a support 81 and three spaced U-shaped straps 82 for securing the thumb to the support 81. The conventional fastening device can be manufactured based on personal order. However, its tolerance is great especially for the thumb of a young child. Thus, its fastening effect is poor. Further, cotton is formed around the support 81 for flexibility purposes. Thus, it tends to cause the thermal damage for the thumb. Furthermore, the fastening of the U-shaped straps 82 on the thumb may be either too tight or too loose. Thus, the need for improvement still exists.

SUMMARY OF THE INVENTION

It is therefore one object of the invention to provide a device for fastening a thumb and a method therefor having the advantages including customized 3D printing having high precision and convenience, single hand handed operation, and non-binding correction having high performance. Particularly, the invention aims to solve the problems associated with the conventional art below. The conventional fastening device can be manufactured based on personal order. However, its tolerance is great especially for the thumb of a young child. Thus, its fastening effect is poor. Further, cotton is formed around the support for flexibility purposes. Thus, it tends to cause the thermal damage for the thumb. Furthermore, the fastening of the U-shaped straps on the thumb may be either too tight or too loose due to improper use.

For achieving above and other objects, the invention provides a device for fastening a thumb, the device being formed integrally and comprising a first tubular member including a first elliptical hole having a first major axis and a first minor axis; a second tubular member including a second elliptical hole having a second major axis and a second minor axis wherein length of the second major axis is greater than that of the first major axis and the second major axis is perpendicular to the first major axis so that the second elliptical hole is perpendicular to the first elliptical hole and length of the second minor axis is greater than that of the first minor axis; and a joint interconnecting the first tubular member and the second tubular member and including a fastener; wherein the device for fastening a thumb is configured to dispose on the thumb having a distal phalanx, a proximal phalanx, and an interphalangeal joint; wherein when the device for fastening a thumb is disposed on the thumb, the first tubular member is disposed on the distal phalanx, the second tubular member is disposed on the proximal phalanx, and the fastener presses the interphalangeal joint to prevent the interphalangeal joint from being bent; and wherein the device for fastening a thumb is fastened by the distal phalanx after has disposed on the thumb.

The invention further provides a method for fastening a thumb, the method being tied to the above device, the method comprising the steps of disposing the device for fastening a thumb on the thumb having a distal phalanx, a proximal phalanx, and an interphalangeal joint wherein the distal phalanx has a distal phalanx major axis and a distal phalanx minor axis, wherein length of the first major axis is greater than or equal to that of the distal phalanx major axis, wherein length of the first minor axis is greater than or equal to that of the distal phalanx minor axis, wherein the interphalangeal joint has a phalanx major axis and a phalanx minor axis, wherein length of the second major axis is greater than that of the phalanx major axis, and length of the second minor axis is greater than that of the phalanx major axis and less than that of the phalanx minor axis; aligning the second major axis of the device for fastening a thumb with the phalanx major axis; disposing the device for fastening a thumb on the thumb wherein the second major axis of the second tubular member passes through the distal phalanx major axis and the phalanx major axis; rotating the device for fastening a thumb 90-degree after the second major axis of the second tubular member has passed through the phalanx major axis; disposing the first tubular member on the distal phalanx so that the second tubular member is disposed on the proximal phalanx and the fastener presses the interphalangeal joint to prevent the interphalangeal joint from being bent; and using the device for fastening a thumb to straighten the thumb for correction.

The above and other objects, features and advantages of the invention will become apparent from the following detailed description taken with the accompanying drawings.

DETAILED DESCRIPTION OF THE INVENTION

Figure 1:
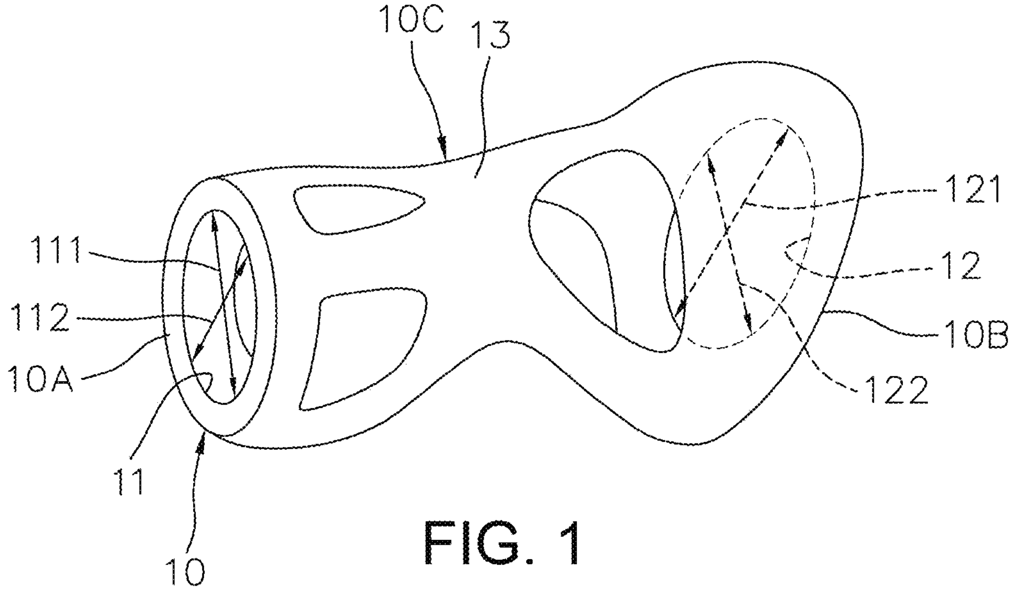
FIG. 1 is a perspective view of a device for fastening a thumb according to a preferred embodiment of the invention, viewed from a first angle.

Referring to FIGS. 1, 2, 3 and 7, a device 10 for fastening a thumb in accordance with a preferred embodiment of the invention is shown. The device 10 for fastening a thumb is formed integrally and comprises the following components as discussed in detail below.

A first tubular member 10A includes a first elliptical hole 11 having a first major axis 111 and a first minor axis 112.

A second tubular member 10B includes a second elliptical hole 12 having a second major axis 121 and a second minor axis 122. A length of the second major axis 121 is greater than that of the first major axis 111. The second major axis 121 is perpendicular to the first major axis 111 so that the second elliptical hole 12 is perpendicular to the first elliptical hole 11. A length of the second minor axis is greater than that of the first minor axis 112.

A joint 10C interconnects the first tubular member 10A and the second tubular member 10B and includes a fastener 13.

Thereby, the device 10 for fastening a thumb is configured to dispose on the thumb 90 which has a distal phalanx 91, a proximal phalanx 93 and an interphalangeal joint 92. When the device 10 for fastening a thumb is disposed on the thumb 90, the first tubular member 10A is disposed on the distal phalanx 91, the second tubular member 10B is disposed on the proximal phalanx 93, and the fastener 13 presses the interphalangeal joint 92 to prevent the interphalangeal joint 92 from being bent. Therefore, the device 10 for fastening a thumb may be used to straighten the thumb 90 for correction.

Practically, the device 10 for fastening a thumb is an integral part formed by 3D printing. The device 10 for fastening a thumb is fastened by the interphalangeal joint 92 after has disposed on the thumb 90.

Length of the first major axis 111 is preferably 1.1 to 1.5 times greater than that of the first minor axis 112. Ratio of the length of the first major axis 111 to that of the first minor axis 112 is obtained based on ratio of width of the thumb to height of the thumb of human being. The ratio is well-known in medicine.

Figure 8:
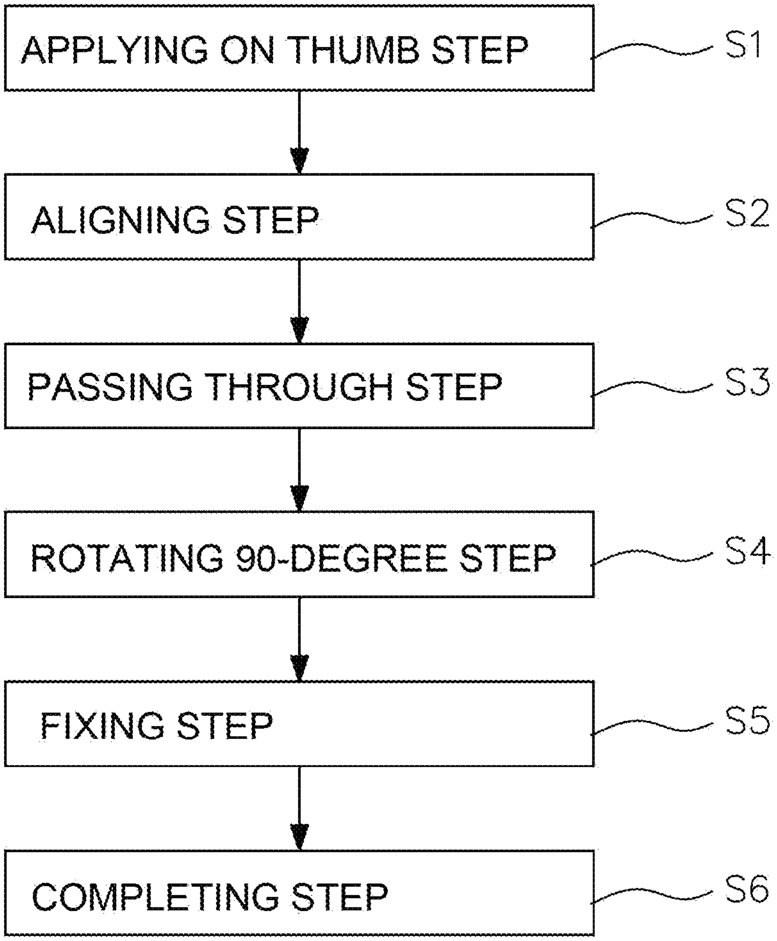
FIG. 8 is a flow chart illustrating a method for fastening a thumb according to the invention.
Figure 9:
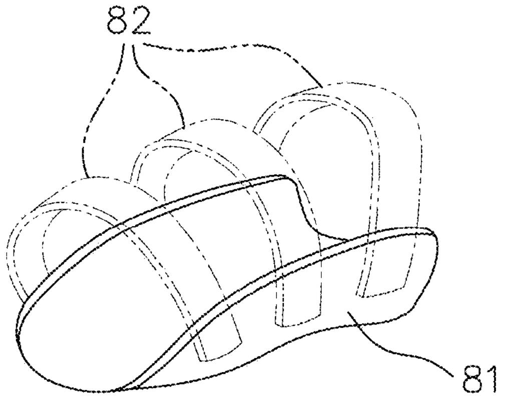
FIG. 9 (PRIOR ART)
FIG. 9 is a perspective view of a conventional device for fastening a thumb.

Referring to FIG. 8, a method for fastening a thumb in accordance with the invention is illustrated. The method is tied to the device 10 for fastening a thumb discussed above and comprises the steps as discussed in detail below.

Figure 2:
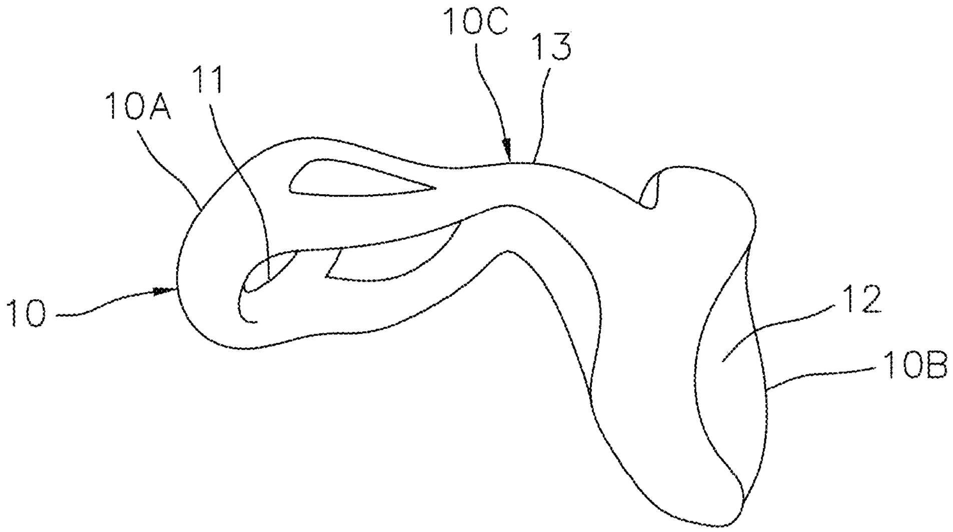
FIG. 2 is a perspective view of the device for fastening a thumb according to the preferred embodiment of the invention, viewed from a second angle.
Figure 3:
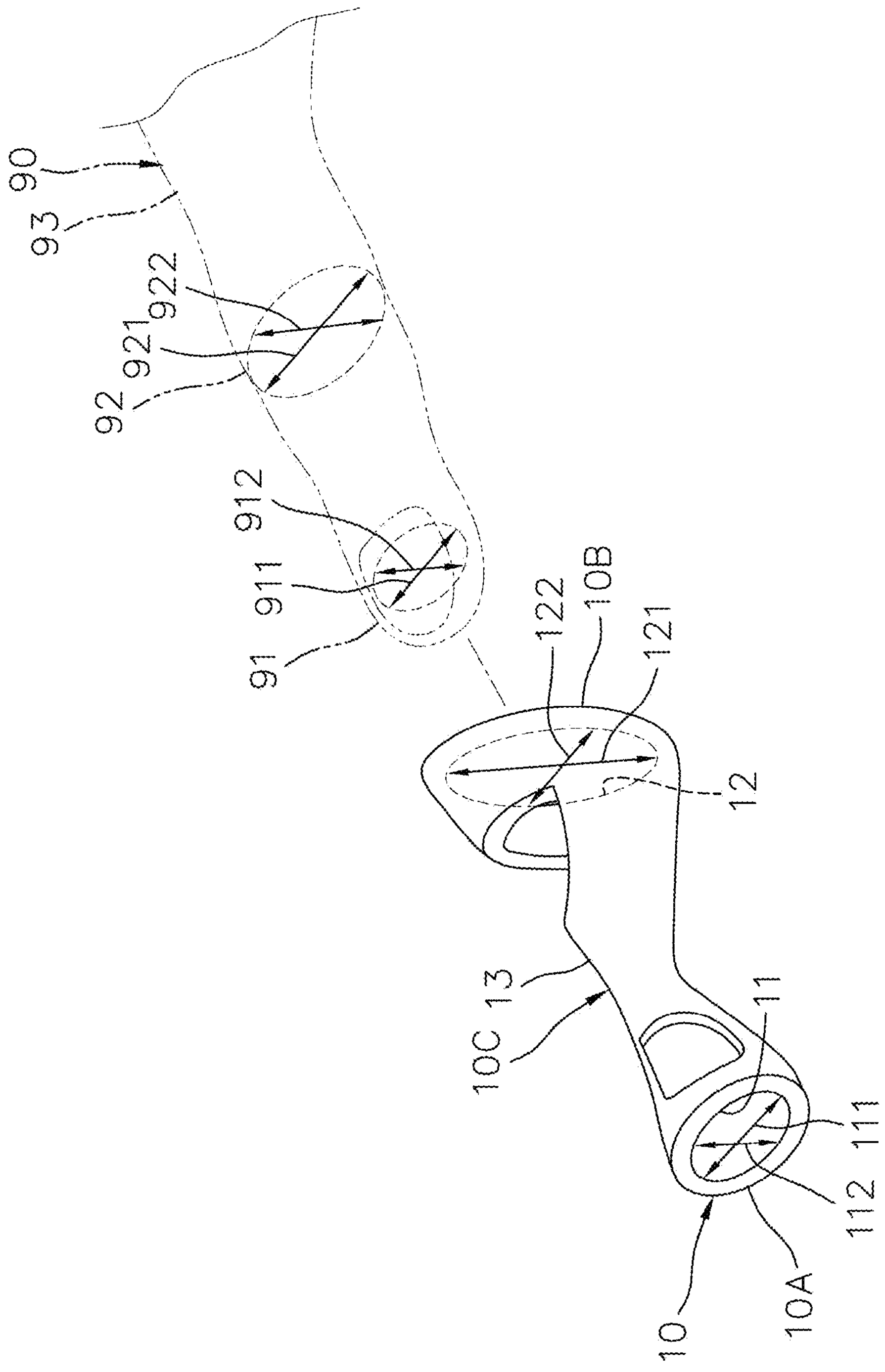
FIG. 3 is a perspective view of the device for fastening a thumb being ready to correct the thumb of a patent.
Figure 4:
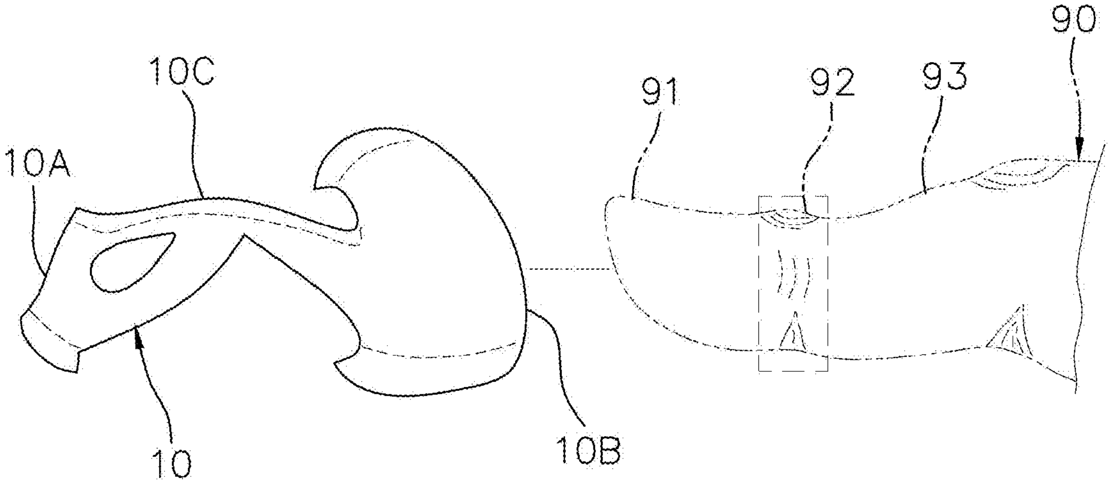
FIG. 4 is a perspective view of the device for fastening a thumb being ready to correct the thumb of the patent in a first fastening step.
Figure 5:
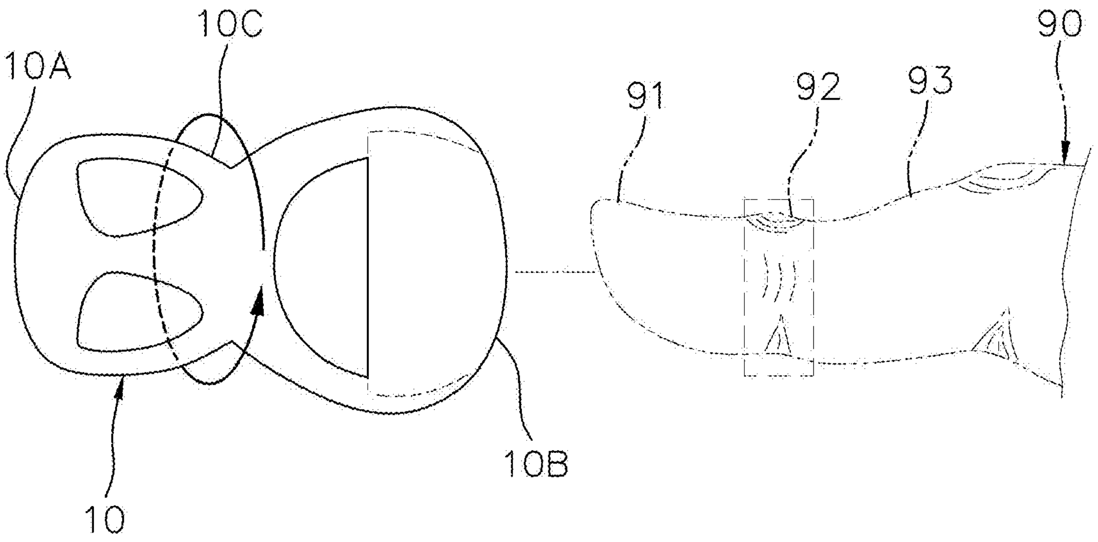
FIG. 5 is a perspective view of the device for fastening a thumb being ready to correct the thumb of the patent in a second fastening step.

Referring to FIG. 8 in conjunction with FIGS. 1, 2 and 3, step S1 (briefly referred as applying on thumb step) of disposing the device 10 for fastening a thumb on the thumb 90 having a distal phalanx 91, a proximal phalanx 93 and an interphalangeal joint 92. The distal phalanx 91 has a distal phalanx major axis 911 and a distal phalanx minor axis 912. Length of the first major axis 111 is greater than or equal to that of the distal phalanx major axis 911. Length of the first minor axis 112 is greater than or equal to that of the distal phalanx minor axis 912. The interphalangeal joint 92 has a phalanx major axis 921 and a phalanx minor axis 922. Length of the second major axis 121 is greater than that of the phalanx major axis 921. Length of the second minor axis 122 is greater than that of the phalanx major axis 921.

Referring to FIG. 8 in conjunction with FIGS. 2 to 5, step S2 (briefly referred as aligning step) of aligning the second major axis 121 of the device 10 for fastening a thumb with the phalanx major axis 921.

Figure 6A:
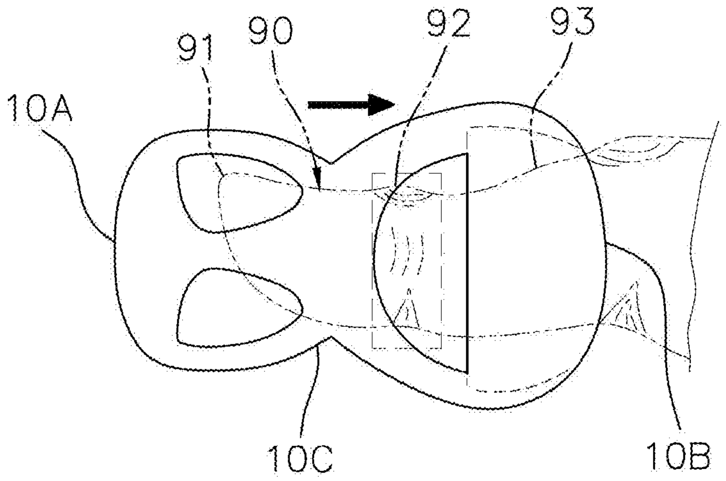
FIG. 6A is a perspective view of the device for fastening a thumb being ready to correct the thumb of the patent in a third fastening step, viewed from a first angle.
Figure 6B:
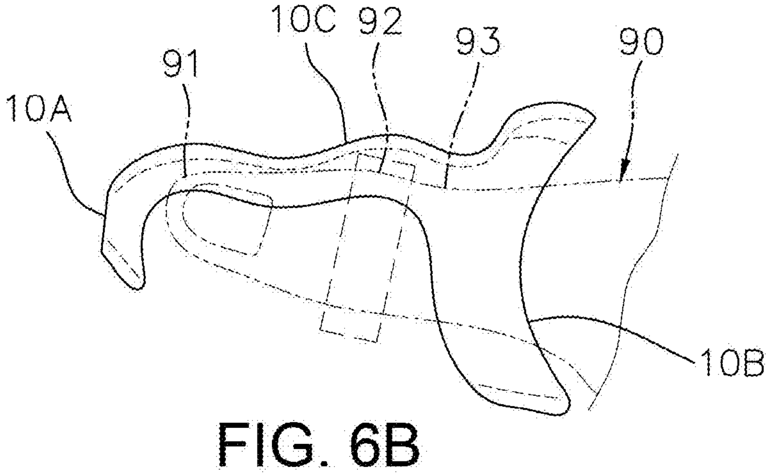
FIG. 6B is a perspective view of the device for fastening a thumb being ready to correct the thumb of the patent in the third fastening step, viewed from a second angle.

Referring to FIG. 8 in conjunction with FIGS. 6A and 6B, step S3 (briefly referred as passing through step) of disposing the device 10 for fastening a thumb on the thumb 90 in which the second major axis 121 of the second tubular member 10B passes through the distal phalanx major axis 911 and the phalanx major axis 921.

Referring to FIG. 8, step S4 (briefly referred as rotating 90-degree step) of rotating the device 10 for fastening a thumb 90-degree after the second major axis 121 of the second tubular member 10B has passed through the phalanx major axis 921.

Figure 7:
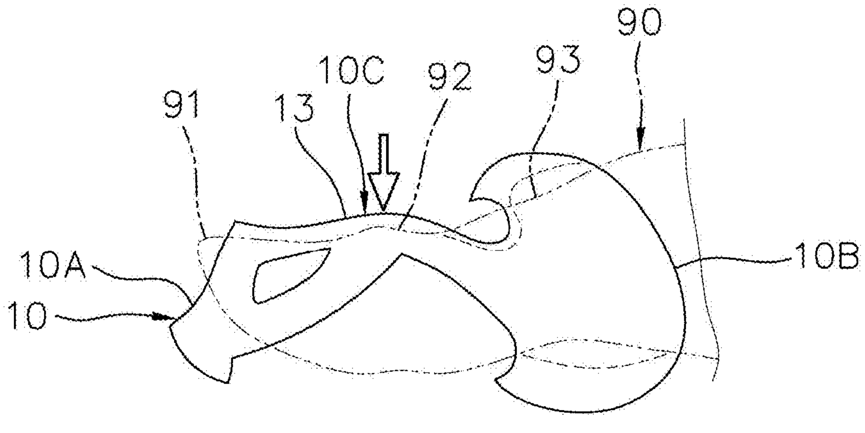
FIG. 7 is a perspective view of the device for fastening a thumb being ready to correct the thumb of the patent in a fourth fastening step.

Referring to FIG. 8 in conjunction with FIG. 7, step S5 (briefly referred as fixing step) of disposing the first tubular member 10A on the distal phalanx 91 so that the second tubular member 10B is disposed on the proximal phalanx 93 and the fastener 13 presses the interphalangeal joint 92 to prevent the interphalangeal joint 92 from being bent.

Referring to FIG. 8, step S6 (briefly referred as completing step) of using the device 10 for fastening a thumb to straighten the thumb 90 for correction.

Practically, the device 10 for fastening a thumb is an integral part formed by 3D printing and length of the first major axis is 1.1 to 1.5 times greater than that of the first minor axis.

Characteristics of the invention are summarized as follows.

The first tubular member 10A includes the first elliptical hole 11. The second tubular member 10B includes the second elliptical hole 12. The second major axis 121 is perpendicular to the first major axis 111 (i.e., specifically the second major axis 121 is perpendicular to the first major axis 111).

The first elliptical hole 11 has the first major axis 111 and the first minor axis 112. The second elliptical hole 12 has the second major axis 121 and the second minor axis 122. Length of the second major axis 121 is greater than that of the first major axis 111. Length of the second minor axis 122 is greater than that of the first minor axis 112.

The distal phalanx 91 has the distal phalanx major axis 911 and the distal phalanx minor axis 912. Length of the first major axis 111 is greater than or equal to that of the distal phalanx major axis 911. Length of the first minor axis 112 is greater than or equal to that of the distal phalanx minor axis 912. The interphalangeal joint 92 has the phalanx major axis 921 and the phalanx minor axis 922. Length of the second major axis 121 is greater than that of the phalanx major axis 921. Length of the second minor axis 122 is greater than that of the phalanx major axis 921 and less than that of the phalanx major axis 921.

Referring to FIGS. 4, 5, 6A, 6B and 7, in view of the above three paragraphs, aligning the second thumb 121 with the phalanx major axis 921, disposing the second tubular member 10B on the interphalangeal joint 92, rotating the device 10 for fastening a thumb 90-degree, and disposing the first tubular member 10A on the distal phalanx 91, the second tubular member 10B is fastened by the interphalangeal joint 92 and disposed on the proximal phalanx 93 because the length of the second minor axis 122 is less than that of the phalanx major axis 921. Additional fastener are not required and it is very convenient.

It is well-known that straightening therapy and support fastening therapy are used to heal the thumb of a young child between one and two years old. Both therapies can improve the thumb movement and decrease trigger. Taking support fastening as an example, it is understood that a support fastening device is required to be manufactured based on personal order and strap bound. It is very inconvenient in use. For overcoming the drawbacks of the conventional art, the invention uses the well-known 3D printing to greatly increase precision and convenience of customization. The integral device for fastening a thumb can be operated by a single hand. In short, steps of aligning the second major axis with the phalanx major axis, disposing the device on the thumb, rotating the device, and disposing the first tubular member on the distal phalanx are performed to fasten the second tubular member. There is no problem of either too tight or too loose.

In addition, in view of the drawings broken lines are used to depict the interphalangeal joint 92 and this means that the second tubular member 10B passes through the interphalangeal joint 92. Also, the fastener 13 presses the interphalangeal joint 92.

The invention has the following advantages and benefits in comparison with the conventional art:

The customized 3D printing has high precision and is convenient. The invention uses the well-known 3D printing to manufacture the device for fastening a thumb based on personal order. The invention has high precision and is convenient. Problem of great tolerance of the conventional support fastening device is eliminated. Thus, the customized 3D printing used by the invention has high precision and is convenient.

Single handed operation and convenience. A user may use one hand to hold the device for fastening a thumb to dispose the device on the thumb, rotate the device, and dispose the first tubular member on the distal phalanx to finish the operation. It is convenient. It is not easy for a toddler to detach the device from the thumb. Thus, the device can be operated by the single hand and is very convenient.

Non-binding correction has high performance. The device for fastening a thumb is formed integrally and includes the first tubular member, the second tubular member and the joint interconnects the first tubular member and the second tubular member. When the first tubular member is disposed on the distal phalanx, the second tubular member is disposed on the proximal phalanx, and the fastener presses the interphalangeal joint to prevent the interphalangeal joint from being bent. Therefore, the device for fastening a thumb may be used to straighten the thumb for correction. Thus, non-binding correction of the device for fastening a thumb has high performance.

While the invention has been described in terms of preferred embodiments, those skilled in the art will recognize that the invention can be practiced with modifications within the scope of the appended claims.

What is claimed is:

1. A method for fastening a thumb comprising the steps of:

providing a device for fastening a thumb, the device for fastening the thumb being formed integrally and comprising:

a first tubular member including a first elliptical hole having a first major axis and a first minor axis;

a second tubular member including a second elliptical hole having a second major axis and a second minor axis wherein a length of the second major axis is greater than that of the first major axis and the second major axis is perpendicular to the first major axis so that the second elliptical hole is perpendicular to the first elliptical hole and a length of the second minor axis is greater than that of the first minor axis; and a joint interconnecting the first tubular member and the second tubular member and including a fastener;

wherein the device for fastening the thumb is configured to dispose on the thumb having a distal phalanx, a proximal phalanx, and an interphalangeal joint; wherein when the device for fastening the thumb is disposed on the thumb, the first tubular member is disposed on the distal phalanx, the second tubular member is disposed on the proximal phalanx, and the fastener presses the interphalangeal joint to prevent the interphalangeal joint from being bent; and wherein the device for fastening the thumb is fastened by the distal phalanx after being disposed on the thumb;

disposing the device for fastening the thumb on the thumb having a distal phalanx, a proximal phalanx, and an interphalangeal joint wherein the distal phalanx has a distal phalanx major axis and a distal phalanx minor axis, wherein the length of the first major axis is greater than or equal to that of the distal phalanx major axis, wherein the length of the first minor axis is greater than or equal to that of the distal phalanx minor axis, wherein the interphalangeal joint has a phalanx major axis and a phalanx minor axis, wherein the length of the second major axis is greater than that of the phalanx major axis, and the length of the second minor axis is greater than that of the phalanx major axis and less than that of the phalanx minor axis;

aligning the second major axis of the device for fastening a thumb with the phalanx major axis;

disposing the device for fastening a thumb on the thumb wherein the second major axis of the second tubular member passes through the distal phalanx major axis and the phalanx major axis;

rotating the device for fastening a thumb 90 degree 90-degrees after the second major axis of the second tubular member has passed through the phalanx major axis;

disposing the first tubular member on the distal phalanx so that the second tubular member is disposed on the proximal phalanx and the fastener presses the interphalangeal joint to prevent the interphalangeal joint from being bent; and using the device for fastening the thumb to straighten the thumb for correction.

2. The method for fastening the thumb of claim 1, wherein the device for fastening the thumb is an integral part formed by 3D printing and the length of the first major axis is 1.1 to 1.5 times greater than that of the first minor axis.

* * * * *